United States Patent [19]
Loeliger

[11] 3,962,311
[45] June 8, 1976

[54] PREPARATION OF CYCLOHEXADIENE COMPOUNDS
[75] Inventor: Peter Loeliger, Pfaffhausen, Switzerland
[73] Assignee: Hoffmann-La Roche Inc., Nutley, N.J.
[22] Filed: Aug. 16, 1974
[21] Appl. No.: 497,993

[30] Foreign Application Priority Data
Aug. 24, 1973 Switzerland.................. 12195/73

[52] U.S. Cl. .................. 260/468 L; 260/586 C
[51] Int. Cl.² ............ C07C 67/30; C07C 45/00; C07B 29/00
[58] Field of Search....... 260/468 L, 586 C, 586 CA

[56] References Cited
UNITED STATES PATENTS
3,531,504  4/1970  Conia.......................... 260/397.4

OTHER PUBLICATIONS
Egger et al., Trans. Faraday Soc. 66, 410 (1970).
March, Advanced Organic Chemistry pp. 834–837, (1968).

Primary Examiner—Robert Gerstl
Attorney, Agent, or Firm—Samuel L. Welt; Bernard S. Leon; Richard A. Gaither

[57] ABSTRACT

Cyclohexadienes are produced by heating in the presence of an organic solvent a compound of the formula:

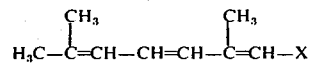

wherein X is either —COCH₃ or —COOR₁, R₁ is a lower alkyl group.

The preferred cyclohexadienes are useful as intermediates in the preparation of odorants.

5 Claims, No Drawings

PREPARATION OF CYCLOHEXADIENE COMPOUNDS

SUMMARY OF THE INVENTION

The present invention is concerned with a process for the manufacture of cyclohexadienes.

The cyclohexadienes which are obtained according to the present process have the following formula:

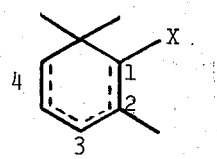

wherein X is selected from the group consisting of —COCH₃ and —COOR₁, R₁ is lower alkyl and the broken lines denote two double-bonds either in the 1- and 3-positions or in the 2- and 4-positions.

According to the present invention, the cyclohexadienes of formula I above are manufactured by heating a compound of the formula:

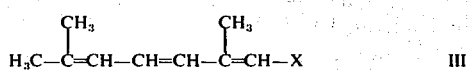

wherein X is as defined above; in the presence of an organic solvent.

The novel process of this invention is considerably less cumbersome than the known processes for the preparation of compounds of the type of those of formula I (see Helv.Chim Acta 54, 1767(1971), ibid. 53, 541(1970), Ber. 74,1242(1941)).

It will be appreciated that formula I above embraces the following two formulae:

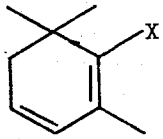 and 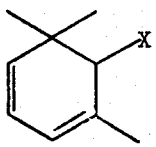

(Ia)                (Ib)

wherein X is as defined above.

DETAILED DESCRIPTION OF THE INVENTION

As used in this description and in the claims appended hereto, the term "lower alkyl" means straight-chain or branched-chain alkyl groups having from 1 to 6 carbon atoms, e.g., methyl, ethyl, isopropyl, hexyl and the like. The ethyl group is the preferred lower alkyl group.

It will also be appreciated that formula II above includes all possible cis- and trans-isomers which can occur by virtue of the presence of the C=C double-bonds.

The cyclization of a compound of formula II in accordance with the present invention is carried out at a temperature of about 180°C. to about 250°C., preferably at a temperature ranging from about 220°C. to about 240°C. The heating is preferably carried out in an inert atmosphere (e.g., under nitrogen). In carrying out this reaction, any conventional inert organic solvent can be utilized. In fact, the nature of the inert organic solvent is not critical. There are, of course, preferably used high-boiling solvents, namely those having boiling points above about 180°C. Examples of suitable solvents are high-boiling alkanes, e.g, decane, or cycloalkanes, e.g., decalin, as well as diglyme (diethyleneglycol dimethyl ether), polyethyleneglycolether, diethylaniline and the like.

Use of a lower boiling solvent, i.e., one having a boiling point below 180°C. is within the scope of the instant process. The requisite cyclization temperature is achieved by conducting the process in a closed system. Examples of such lower-boiling solvents are aliphatic hydrocarbons such as hexane and aromatic hydrocarbons such as benzene.

The time required to complete the cyclization although not critical is dependent on the temperature. Increased yields are realized when the cyclization is carried out at about 230°C. over a period of about 10 hours. Completion of the cyclization of the starting material, i.e., formula I, to cyclohexadiene can be determined analytically, for example, by gas chromatography. The cyclohexadienes of formula I are normally obtained as a mixture of the isomers of formulae Ia and Ib above.

If desired, the isomer mixture can be separated into the individual components by known techniques. A preferred method of separation of the isomeric mixture is by chromatography on silica gel. While standard eluants may be used to achieve the silica gel chromatography, a preferred eluant is a mixture of 5% ethyl ether in hexane (by volume).

The cyclohexadiens of formulae Ia and Ib or isomeric mixtures thereof are useful as intermediates for the preparation of odorants, for example, the damascenones

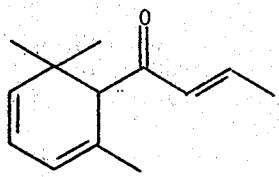

α-damascenone and

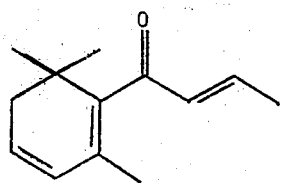

β-damascenone

The conversion into these odorants can be carried out according to known methods, for example, according to Buchi et al., Helv. Chim. Acta 54, (1971), 1767 in the case where X represents a —COOR group, or according to Cookson et al., J.C.S. Chem. Comm. (1973), 1961 in the case where X represents the —COCH₃ group, the disclosures of which are incorporated herein by reference.

The starting materials of formula II above are well known and can be prepared by known procedures.

The following non-limiting examples illustrate the present invention.

EXAMPLE 1

30.0 g. (0.137 mol) of 3,7-dimethyl-2,4,6-octatrienoic acid ethyl ester (J. N. Nazarov et al., Zhur. Obshschei Khim. 28, 460–74 (1958), C. A. 52, 13612 c) are dissolved in 400 ml. of diethylaniline and melted down in 3 Pyrex glass cylinders (each of 150 ml. volume) under a high vacuum. The cylinders are heated at 250°C. for 14 hours, cooled and the contents taken up in ether and poured on to 2-N hydrochloric acid. The ether phase is washed several times with 2-N hydrochloric acid and then dried with anhydrous sodium sulphate. After concentration on a rotary evaporator, there are obtained 29.4 g. of a brown oil which is distilled under a high vacuum. There are thus obtained 23.6 g. (79% of theory) of 2,6,6-trimethyl-1,3-(and 2,4)-cyclohexadiene-1-carboxylic acid ethyl ester as a colorless oil of boiling point 54°–57°C/0.5 mmHg. Gas chromatographic analysis shows that the two isomers are present in the ratio 2:1 (1,3-:2,4-cyclohexadienyl grouping). 4.5 g. of the product obtained are chromatographed on a hundredfold amount of silica gel (eluant: hexane/0.5% ether). There are obtained 1.9 g. of 2,6,6-trimethyl-1,3-cyclohexadiene-1-carboxylic acid ethyl ester (β-safranyl ethyl ester), UV: $\lambda_{max}$ 274nm ($\epsilon$ = 5700), and 0.9 g. of 2,6,6-trimethyl-2,4-cyclohexadiene-1-carboxylic acid ethyl ester (α-safranyl ethyl ester), UV: $\lambda_{max}$ 270 nm ($\epsilon$ = 4200).

EXAMPLE 2

14.4 g. (0.088 mol) of 4,8-dimethyl-nona-3,5,7-trien-2-one are dissolved in 200 ml. of diethylaniline and melted down under a high vacuum in 2 Pyrex glass tubes. The tubes are heated at 250°C. for 2 hours, cooled and the contents taken up in ether and poured on to 2-N hydrochloric acid. The ether phase is washed several times with 2-N hydrochloric acid and dried over anhydrous sodium sulphate. After concentration on a rotary evaporator, there are obtained 14.4 g. of a brown oil which is distilled by means of a bulb tube oven under a high vacuum. 9.3 g. (65% of theory) of 1-acetyl-2,6,6-trimethyl-1,3-(and 2,4)-cyclohexadiene distill as a colorless oil at an oven temperature of 70°C. (0.01 mmHg). Gas-chromatographic analysis shows that the two isomers are present in the ratio ca 1:1 (1,3-:2,4-cyclohexadienyl grouping). A portion of the isomer mixture is separated into the following two components by preparative gas chromatography:

1-acetyl-2,6,6-trimethyl-1,3-cyclohexadiene, UV: $\lambda_{max}$ 278 nm ($\epsilon$ = 3000);

1-acetyl-2,6,6-trimethyl-2,4-cyclohexadiene, UV: $\lambda_{max}$ 266 nm ($\epsilon$ = 3800), 320 nm ($\epsilon$ = 1300).

I claim:

1. A process for the manufacture of an isomeric mixture of cyclohexadienes of the formulae:

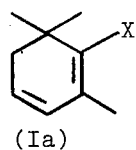 and 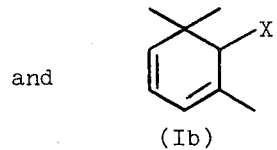

(Ia)          (Ib)

wherein X is selected from the group consisting of —COCH₃ and —COOR₁, R₁ is a lower alkyl group having from 1 to 6 carbon atoms; which process comprises heating a compound of the formula:

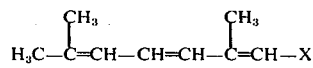

wherein X is as defined above; in the presence of an inert organic solvent and at a temperature of from about 180°C. to about 250°C.

2. A process according to claim 1 wherein the heating is carried out at a temperature of about 220°C. to about 240°C.

3. A process according to claim 1 wherein said compound is 3,7-dimethyl-2,4,6-octatrienoic acid ethyl ester.

4. A process according to claim 1 wherein said compound is 4,8-dimethyl-nona-3,5,7-trien-2-one.

5. A process according to claim 1 wherein the organic solvent is selected from the group consisting of decane, decalin, diethyleneglycol dimethyl ether, polyethyleneglycolether and diethylaniline.

* * * * *